United States Patent [19]

Ehrenfreund

[11] 4,310,548
[45] Jan. 12, 1982

[54] PESTICIDAL N-TETRAFLUOROPHENYL-N'-BENZOYL UREAS

[75] Inventor: Josef Ehrenfreund, Allschwil, Sweden

[73] Assignee: Ciba-Geigy Corporation, Ardsley, N.Y.

[21] Appl. No.: 114,912

[22] Filed: Jan. 24, 1980

[30] Foreign Application Priority Data

Feb. 1, 1979 [SE] Sweden ................................. 79981
Oct. 22, 1979 [SE] Sweden ............................... 799453

[51] Int. Cl.³ .................... A01N 47/28; C07C 127/00
[52] U.S. Cl. ....................................... 424/322; 564/44
[58] Field of Search .................... 424/322; 260/553 E; 564/44

[56] References Cited

U.S. PATENT DOCUMENTS

| | | | |
|---|---|---|---|
| 3,989,842 | 11/1976 | Wellinga et al. | 424/273 |
| 4,005,223 | 11/1977 | Sirrenberg et al. | 424/322 |
| 4,085,226 | 4/1978 | Sirrenberg et al. | 424/322 |
| 4,089,975 | 5/1978 | Wade et al. | 424/322 |
| 4,139,636 | 2/1979 | Sirrenberg et al. | 424/322 |
| 4,162,330 | 7/1979 | Ehrenfreund | 424/322 |
| 4,170,657 | 10/1979 | Rigterink | 424/322 |

FOREIGN PATENT DOCUMENTS

| | | |
|---|---|---|
| 832304 | 2/1976 | Belgium . |
| 844066 | 7/1976 | Belgium . |
| 843906 | 1/1977 | Belgium . |
| 2123236 | 12/1971 | Fed. Rep. of Germany . |
| 2601780 | 1/1976 | Fed. Rep. of Germany . |
| 2504982 | 8/1976 | Fed. Rep. of Germany . |
| 2537413 | 3/1977 | Fed. Rep. of Germany . |
| 2726684 | 1/1979 | Fed. Rep. of Germany . |
| 1324293 | 7/1973 | United Kingdom . |
| 1460410 | 1/1977 | United Kingdom . |
| 1488644 | 10/1977 | United Kingdom . |
| 1492364 | 11/1977 | United Kingdom . |
| 1492365 | 11/1977 | United Kingdom . |

OTHER PUBLICATIONS

Wellinga et al., J. Agr. Food Chem., vol. 21, No. 3, 1973, pp. 348–353.

Primary Examiner—Allen J. Robinson
Attorney, Agent, or Firm—John P. Spitals; Frederick H. Rabin

[57] ABSTRACT

Novel substituted N-tetrafluorophenyl-N-'-halobenzoylureas of the formula

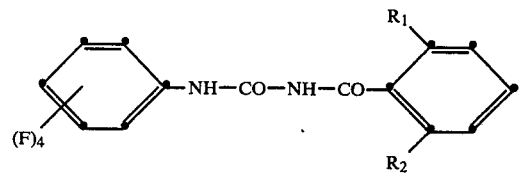

wherein $R_1$ is fluorine or chlorine, and $R_2$ is hydrogen, fluorine or chlorine; processes for producing these compounds, as well as compositions containing them, for combating pests, particularly insects which infest plants and animals. The novel compounds also exhibit an action inhibiting eating in the case of insects damaging plants by eating, and these compounds have favorable ovicidal and ovolarvicidal properties.

8 Claims, No Drawings

PESTICIDAL N-TETRAFLUOROPHENYL-N'-BENZOYL UREAS

The present invention relates to novel N-tetrafluorophenyl-N'-halobenzoylureas, to processes for producing them, and to their use in controlling pests.

The substituted N-tetrafluorophenyl-N'-halobenzoylureas according to the invention have the formula I

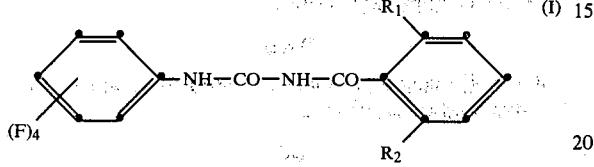

wherein $R_1$ is fluorine or chlorine, and $R_2$ is hydrogen, fluorine or chlorine.

Compounds according to the invention which are preferred by virtue of their activity as pesticidal active substances are the compounds of the formula Ia

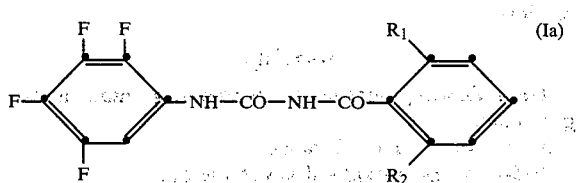

wherein $R_1$ and $R_2$ have the meanings defined above.

To be particularly emphasised on account of its good insecticidal effectiveness is the compound according to the invention, which compound has the formula

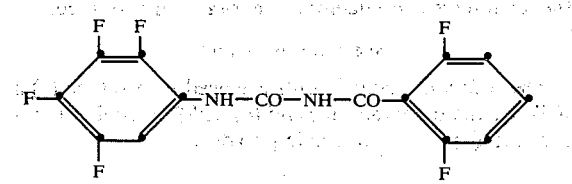

The compounds of the formula I can be produced by known methods (see, inter alia, the German Offenlegungsschriften Nos. 2,123,236 and 2,601,780).

A compound of the formula I can thus be obtained for example by reacting
(a) a compound of the formula II

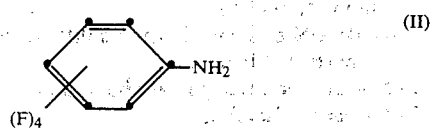

with a compound of the formula III

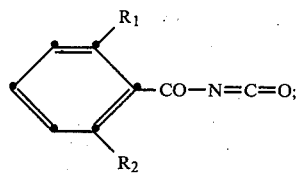

or
(b) a compound of the formula IV

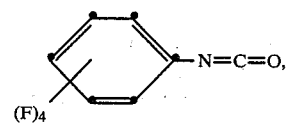

optionally in the presence of a basic substance, with a compound of the formula V

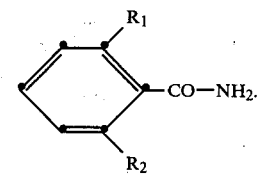

In the above formulae II, III, IV and V, the radicals $R_1$ and $R_2$ have the meanings given under the formulae I and Ia.

The processes (a) and (b) mentioned are preferably performed under normal pressure and in the presence of an organic solvent or diluent. Suitable solvents or diluents are for example: ethers and ethereal compounds, such as diethyl ether, dipropyl ether, dibutyl ether, dioxane, dimethoxyethane and tetrahydrofuran; N,N-dialkylated carboxylic acid amides; aliphatic, aromatic as well as halogenated hydrocarbons, particularly benzene, toluene, xylene, chloroform, methylene chloride, carbon tetrachloride and chlorobenzene; nitriles such as acetonitrile or propionitrile; dimethylsulfoxide, and also ketones, for example acetone, methyl ethyl ketone, methylisopropyl ketone and methylisobutyl ketone. In general, process (a) is performed at a temperature of −10° to 100° C., preferably between 15° and 25° C., optionally in the presence of an organic base, for example triethylamine. Process (b) is performed at a temperature of 0° to 150° C., preferably at the boiling point of the solvent used, and optionally in the presence of an organic base, such as pyridine, and/or with the addition of an alkali metal or alkaline-earth metal salt, preferably sodium.

The starting materials of the formulae II, III, IV and V are known, or can be produced by processes analogous to known processes. For example, the tetrafluoroisocyanates of the formula IV are obtainable by phosgenation of the corresponding tetrafluoroanilines of the formula II using in general customary processes.

It is already known that specific N-phenyl-N'-benzoylureas have insecticidal properties (see German Offenlegungsschriften Nos. 2,123,236, 2,504,982, 2,531,279, 2,537,413, 2,601,780 and 2,726,684, and also the Belgian Patent Specifications Nos. 832,304, 843,906 and 844,066).

It has now been found that surprisingly the N-tetrafluorophenyl-N'-halobenzoylureas of the formula I according to the invention, whilst having good tolerance to plants and negligible toxicity to warm-blooded animals, have excellent activity as pesticidal active substances. They are suitable in particular for combating pests which infest plants and animals.

The compounds of the formula I are especially suitable for combating insects of the orders: Lepidoptera, Coleoptera, Homoptera, Heteroptera, Diptera, Thysanoptera, Orthoptera, Anoplura, Siphonaptera, Mallophage, Thysanura, Isoptera, Psocoptera and Hymenoptera.

By virtue of their very favourable action as ovicidal and ovolarvicidal active substances, the compounds of the formula I are suitable also for combating insects which damage plants by eating, in crops of ornamental plants and useful plants, especially in cotton crops (for example against Spodoptera littoralis and Heliothis virescens) and in crops of vegetables (for example against Leptinotarsa decemlineata). The compounds of the formula I are characterised by a marked activity against larval insect stages and insect eggs, particularly against larval stages and eggs of insects which damage plants by eating. When compounds of the formula I are taken with the food by adult insects, there can be observed in many cases, especially with Coleoptera, for example Anthonomus grandis, a reduced oviposition and/or a reduced hatching rate.

The compounds of the formula I are moreover suitable for combating ectoparasites in domestic animals and in productive animals, for example by treatment of animals, livestock housing and pasture land.

The action of the compounds according to the invention or of compositions containing them can be considerably widened and adapted to suit prevailing conditions by the addition of other insecticides. Suitable additives are for example the following active substances:
organic phosphorus compounds,
nitrophenols and derivatives,
formamidines, ureas,
carbamates and
chlorinated hydrocarbons.

The compounds of the formula I can be combined with particular advantage also with substances which have a pesticidally intensifying effect. Examples of such compounds are, inter alia: piperonylbutoxide, propynyl ethers, propynyl oximes, propynyl carbamates and propynyl phosphonates, 2-(3,4-methylenedioxyphenoxy)-3,6,9-trioxaundecane or S,S,S-tributylphosphorotrithioates.

The compounds of the formula I can be used on their own or together with suitable carriers and/or additives. Suitable carriers and additives may be solid or liquid and correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays, solutions or suspensions, the formulation of these preparations being effected in a manner commonly known in the art. Also to be mentioned are cattle dips and spray races, in which aqueous preparations are used. These forms of preparation are particularly suitable for combating zooparasitic pests.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:
solid preparations: dusts, scattering agents or granulates (coated granules, impregnated granules and homogeneous granules);
liquid preparations:
(a) water-dispersible concentrates of active substance; wettable powders, pastes or emulsions;
(b) solutions.

The content of active substance in the described compositions is between 0.1 and 95%.

The active substances of the formula I can be formulated for example as follows:

Dusts

The following substances are used to produce (a) a 5% dust and (b) a 2% dust:

(a)

5—parts of active substance, and
95—parts of talcum;

(b)

2—parts of active substance,
1—part of highly dispersed silicic acid, and
97—parts of talcum.

The active substance is mixed and ground with the carriers.

Granulate

The following ingredients are used to produce a 5% granulate:
5—parts of active substance,
0.25—part of epoxidised vegetable oil,
0.25—part of cetyl polyglycol ether,
3.50—parts of polyethylene glycol, and
91—parts of kaolin (particle size 0.3–0.8 mm).

The active substance is mixed with epoxidised vegetable oil and dissolved in 6 parts of acetone, and the polyethylene glycol and cetyl polyglycol ether are then added. The solution obtained is sprayed onto kaolin and the acetone is subsequently evaporated off in vacuo.

Wettable powders

The following constituents are used to produce (a) a 40% wettable powder, (b) and (c) a 25% wettable powder, and (d) a 10% wettable powder:

(a)

40—parts of active substance,
5—parts of sodium lignin sulfonate,
1—part of sodium dibutyl-naphthalene sulfonate, and
54—parts of silicic acid;

(b)

25—parts of active substance,
4.5—parts of calcium lignin sulfonate,
1.9—parts of Champagne chalk/hydroxyethyl cellulose mixture (1:1),
1.5—parts of sodium dibutyl-naphthalene sulfonate,
19.5—parts of silicic acid,
19.5—parts of Champagne chalk, and
28.1—parts of kaolin;

(c)

25—parts of active substance, 2.5—parts of isooctylphenoxy-polyoxyethyleneethanol,
1.7—parts of Champagne chalk/hydroxyethyl cellulose mixture (1:1),
8.3—parts of sodium aluminium silicate,
16.5—parts of kieselgur, and
46—parts of kaolin;

(d)

10—parts of active substance,
3—parts of a mixture of the sodium salts of saturated fatty alcohol sulfates,
5—parts of naphthalenesulfonic acid/formaldehyde condensate, and
82—parts of kaolin.

The active substance is intimately mixed in suitable mixers with the additives, and the mixture is then ground in the appropriate mills and rollers to obtain wettable powders which can be diluted with water to give suspensions of the desired concentration.

Emulsifiable concentrates

The following substances are used to produce (a) a 10% emulsifiable concentrate, (b) a 25% emulsifiable concentrate and (c) a 50% emulsifiable concentrate:

(a)

10—parts of active substance,
3.4—parts of epoxidised vegetable oil,
3.4—parts of a combination emulsifier consisting of fatty alcohol polyglycol ether and alkylaryl sulfonate calcium salt,
40—parts of dimethylformamide, and
43.2—parts of xylene;

(b)

25—parts of active substance,
2.5—parts of epoxidised vegetable oil,
10—parts of an alkylarylsulfonate/fatty alcohol polyglycol ether mixture,
5—parts of dimethylformamide, and
57.5—parts of xylene;

(c)

50—parts of active substance,
4.2—parts of tributylphenol-polyglycol ether,
5.8—parts of calcium-dodecylbenzenesulfonate,
20—parts of cyclehexanone, and
20—parts of xylene.

Emulsions of the concentration required can be prepared from these concentrates by dilution with water.

Spray

The following constituents are used to produce (a) a 5% spray and (b) a 95% spray:

(a)

5—parts of active substance,
1—part of epoxidised vegetable oil,
94—parts of ligroin (boiling limits 160°–190° C.);

(b)

95—parts of active substance, and
5—parts of epoxidised vegetable oil.

EXAMPLE 1

5.8 g of 2,6-difluorobenzoylisocyanate is added, at room temperature and with the exclusion of moisture, to a solution of 4.95 g of 2,3,4,5-tetrafluoroaniline in 20 ml of absolute ether. The precipitate occurring after a short period is filtered off with suction. Recrystallisation from toluene yields N-2,3,4,5-tetrafluorophenyl-N'-2,6-difluorobenzoylurea having a melting point of 198°–202° C.

EXAMPLE 2

4.95 g of 2,3,4,6-tetrafluoroaniline is dissolved in 20 ml of absolute ether, and to the solution is added, at room temperature and with the exclusion of moisture, 5.8 g of 2,6-difluorobenzoylisocyanate. The precipitate which is formed is filtered off with suction, and recrystallized from toluene to yield N-2,3,4,6-tetrafluorophenyl-N'-2,6-difluorobenzoylurea having a melting point of 178°–182° C.

EXAMPLE 3

The following compounds of the formula I are produced by procedures analogous to those described above:

| (F)$_4$ Position of the F substituents | R$_1$ | R$_2$ | Melting point [°C.] |
|---|---|---|---|
| 2.3.4.5 | Cl | Cl | 215–217 |
| 2.3.4.5 | Cl | H | 199–206 |
| 2.3.4.5 | F | H | 179.5–181 |
| 2.3.4.5 | F | Cl | 213–215 |
| 2.3.4.6 | Cl | Cl | 179–182 |
| 2.3.4.6 | Cl | H | 173–176 |
| 2.3.4.6 | F | H | 152–155 |
| 2.3.4.6 | F | Cl | 179–181 |
| 2.3.5.6 | F | F | 199–200 |
| 2.3.5.6 | Cl | Cl | 182–185 |
| 2.3.5.6 | Cl | H | 174–177 |
| 2.3.5.6 | F | H | 138–145 |
| 2.3.5.6 | F | Cl | 190–194 |

EXAMPLE 4

Action against *Musca domestica*

50 g of freshly prepared CSMA nutrient medium for maggots was weighed off into each of a series of beakers. A specific amount of a 1% (by weight) acetonic solution of the respective active substance was transferred by pipette to the nutrient medium in each beaker. After a thorough mixing of the nutrient medium, the acetone was allowed to evaporate off for at least 20 hours. There were then deposited per active substance and concentration in each case 25 one-day-old *Musca domestica* maggots into each beaker containing the treated nutrient medium. After completion of pupation, the formed pupae were separated from the nutrient medium by flushing with water, and were placed into vessels closed with perforated lids. The pupae flushed out per batch were counted (toxic effect of the active substance on the development of the maggot), and after 10 days the number of flies which had emerged from the pupae was determined.

Compounds according to Examples 1–3 exhibited a good action in the above test.

EXAMPLE 5

Action against *Aedes aegypti*

Sufficient of a 0.1% acetonic solution of the respective active substance was transferred by pipette to the surface of 150 ml of water in a container to obtain concentrations of 10, 5 and 1 ppm in each case. After the acetone had evaporated off, 30-40 two-day-old Aëdes larvae were placed into each container. The mortality rate was ascertained after 1, 2 and 5 days.

Compounds according to Examples 1-3 exhibited in this test a good action against *Aedes aegypti*.

EXAMPLE 6

Ovicidal action on *Heliothis virescens* and *Spodoptera littoralis*

Appropriate proportions of a wettable pulverulent formulation containing 25 percent by weight of the active substance to be tested were in each case diluted with a given amount of water in order to obtain aqueous emulsions having increasing levels of concentration of active substance. One-day-old clusters of eggs of Heliothis and Spodoptera, respectively, deposited on absorbent paper, were immersed for three minutes in the above emulsions containing the active substance, and were then filtered by suction on round filters. The eggs treated in this manner were subsequently laid out in Petri dishes and kept in darkness. After 6 to 8 days, the hatching percentage compared with that of untreated control specimens was determined. The criterion for the evaluation was the minimum concentration of active substance required to effect a 100% destruction of the eggs.

The compounds according to Examples 1-3 exhibited in this test a good ovicidal action against the pests used in the tests.

EXAMPLE 7

Action against *Lucilia sericata*

1 ml of an aqueous solution containing 0.5% of active substance was added to 9 ml of a culture medium at 50° C. About 30 freshly hatched Lucilia sericata maggots were then placed onto the culture medium, and after 48 and 96 hours, respectively, the insecticidal action was determined by ascertaining the mortality rate.

Compounds according to Examples 1-3 exhibited in this test a good action against *Lucilia sericata*.

EXAMPLE 8

Action against *Spodoptera littoralis* (adults)

Vessels each having a volume of 20 liters and each containing three cotton plants about 30 cm in height were sprayed with a solution of the active substance to be tested, until the solution dripped from the plants. The plants treated in this manner were subsequently held for 12 days at 30°-35° C. with 60-70% relative humidity. After this period of time, the vessels were each infested with 10 two- to three-day old females of Spodoptera, and kept for two days at 28° C. with 60% relative humidity.

An evaluation was afterwards made with regard to the mortality rate of the adult lepidopters, the number of eggs laid, and also the extent of eating by the hatched larvae in comparison with these factors in the case of the untreated specimens.

Compounds according to Examples 1-3 exhibited in this test a high level of activity.

EXAMPLE 9

Action against *Spodoptera littoralis* and *Heliothis virescens* (larvae; eating and contact action)

Potted cotton and soya-bean plants about 30 cm high were sprayed dripping wet with a diluted aqueous emulsion preparation of the active substance to be tested. After the drying of the applied coating, the cottom plants were each infested with 5 larvae in the third larval stage of Spodoptera, and the soya-bean plants each with 10 larvae in the third larval stage of Heliothis. The specimens were kept for 5 days in artificial light, at a temperature of about 26° C. with 50-60% relative humidity. The evaluation which followed was made on the basis of percentage mortality, reduction of eating, deformations, and inhibition of development, compared with these results in the case of the untreated control specimens.

The compounds according to Examples 1 to 3 exhibited high activity in this test.

EXAMPLE 10

Action against *Spodoptera littoralis* and *Heliothis virescens* (larvae and eggs)

Three cotton plants about 15-20 cm in height and grown in pots were treated with a sprayable liquid preparation of the active substance to be tested. After the drying of the coating which had been sprayed on, the potted plants were placed into a tin container of about 20 liters capacity, which was covered with a glass plate. The humidity inside the covered container was controlled in a manner ensuring that no condensation water formed. Direct light falling onto the plants was avoided. The three plants were then infested in all with:
(a) 50 larvae of *Spodoptera littoralis* and *Heliothis virescens*, respectively, of the first larval stage;
(b) 20 larvae of *Spodoptera littoralis* and *Heliothis virescens*, respectively, of the third larval stage;
(c) two coatings of eggs of Spodoptera littoralis and *Heliothis virescens*, respectively: for this purpose, 2 leaves of a plant were in each case enclosed in a plexiglass cylinder sealed at each end with gauze; two coatings of eggs of Spodoptera, or a portion of a cotton-plant leaf on which were deposited eggs of Heliothis, were added to the enclosed leaves.

An evaluation, using untreated control plants as a comparison, was made after 4 to 5 days on the basis of the following criteria:
(a) number of living larvae,
(b) inhibition of larval development and shedding,
(c) damage caused by eating (scraping and hole damage),
(d) hatching rate (number of larvae which have emerged from the eggs).

The compounds according to Examples 1 to 3 exhibited a good overall effectiveness in the above test.

EXAMPLE 11

Chemosterilising action against *Anthonomous grandis*

Adult *Anthonomous grandis*, which had been hatched no longer the 24 hours, were transferred, in grups each of 25 beetles, to cages having lattice walls. The cages containing the beetles were then immersed for 5 to 10 seconds in an acetonic solution containing 1.0 percent by weight of the active substance to be tested. After the beetles were again dry, they were placed, for copulation and oviposition, into covered dishes containing feed. Deposited eggs were flushed out with running water two to three times weekly; they were counted, disinfected by being placed for two to three hours in an aqueous disinfectant (such as "Actamer B 100"), and then deposited into dishes containing a suitable larval diet. The eggs were examined after 7 days to determine whether larvae had developed from the deposited eggs.

In order to ascertain the duration of the chemosterilant effect of the active substances tested, the oviposition of the beetles was observed during a period of about four weeks. The evaluation was on the basis of the reduction of the number of eggs laid and hatched larvae in comparison with that of untreated control specimens. Compounds according to Examples 1 to 3 exhibited high activity in this test.

What is claimed is:

1. A compound of the formula

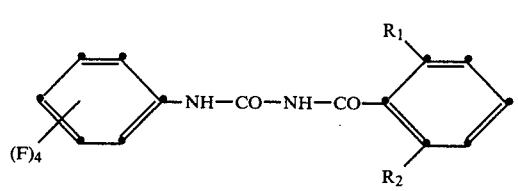

wherein $R_1$ is fluorine or chlorine, and $R_2$ is hydrogen, fluorine or chlorine.

2. A compound according to claim 1

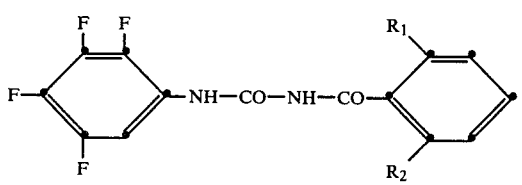

3. The compound according to claim 2 of the formula

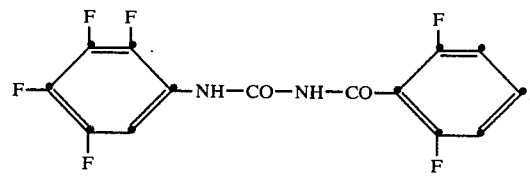

4. The compound according to claim 2 of the formula

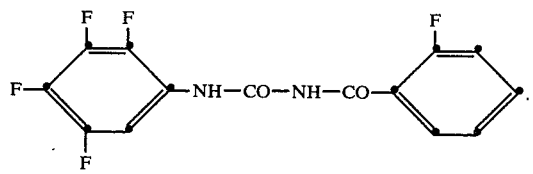

5. The compound according to claim 2 of the formula

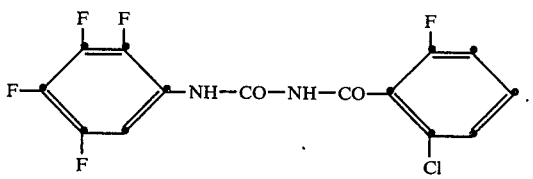

6. The compound according to claim 2 of the formula

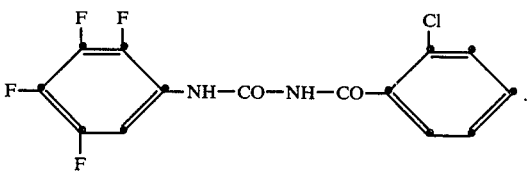

7. An insecticidal composition comprising (1) as active ingredient an insecticidally effective amount of a compound according to claim 1 and (2) a suitable carrier.

8. A method for combatting insects which comprises applying to said insects or to a locus desired to be protected from said insects, an insecticidally effective amount of a compound according to claim 1, 2, 3, 4, 5, or 6.

* * * * *